United States Patent

Kennelly et al.

[11] Patent Number: 4,596,784
[45] Date of Patent: Jun. 24, 1986

[54] CATALYST COMPOSITIONS AND THEIR USE FOR THE PREPARATION OF UNSATURATED CARBOXYLIC ACIDS

[75] Inventors: William J. Kennelly, Newton; Lawrence S. Kirch, Huntington Valley, both of Pa.

[73] Assignee: Rohm and Haas Company, Philadelphia, Pa.

[21] Appl. No.: 693,958

[22] Filed: Mar. 13, 1985

Related U.S. Application Data

[60] Division of Ser. No. 499,108, May 27, 1983, abandoned, which is a continuation-in-part of Ser. No. 385,365, Jun. 7, 1982, abandoned.

[51] Int. Cl.$^4$ .................. B01J 27/198; B01J 21/02; B01J 27/19; B01J 27/192
[52] U.S. Cl. .................. 502/209; 502/206; 502/211; 502/212
[58] Field of Search .............. 502/209, 211, 212, 206

[56] References Cited

U.S. PATENT DOCUMENTS

| | | | |
|---|---|---|---|
| 3,761,516 | 9/1973 | Khoobian | 502/211 X |
| 3,773,692 | 11/1973 | Hensel et al. | 502/242 X |
| 3,795,703 | 3/1974 | Niina et al. | 502/211 X |
| 3,875,220 | 4/1975 | White et al. | 502/206 X |
| 3,998,876 | 12/1976 | Kato et al. | 502/200 X |
| 4,017,423 | 4/1977 | White et al. | 502/211 X |
| 4,051,179 | 9/1977 | Sonobe et al. | 502/211 X |
| 4,070,397 | 1/1978 | White et al. | 502/209 X |
| 4,075,244 | 2/1978 | Akiyama et al. | 502/209 X |
| 4,271,040 | 6/1981 | Khoobian | 502/211 |
| 4,320,227 | 3/1982 | Matsumoto et al. | 562/535 X |
| 4,467,113 | 8/1984 | Matsumoto et al. | 502/209 X |
| 4,489,170 | 12/1984 | Kubetz et al. | 502/211 |
| 4,503,247 | 3/1985 | Khoobian | 502/211 X |
| 4,511,548 | 4/1985 | Attig et al. | 502/212 X |
| 4,558,028 | 12/1985 | Tsunishi et al. | 502/212 X |

FOREIGN PATENT DOCUMENTS 55-122734  3/1979  Japan .................. 502/209

*Primary Examiner*—William G. Wright
*Attorney, Agent, or Firm*—Terence P. Strobaugh

[57] ABSTRACT

Unsaturated carboxylic acids are prepared by the catalytic vapor phase oxidation of unsaturated aldehydes. A novel process for the preparation of these catalysts is disclosed. The catalyst has the following formula:

$$Mo_{12}P_aX^1{}_bV_cAs_dCu_eSb_fX^2{}_gO_x$$

wherein
a–g represent the number of atoms of the particular element depicted;
$X^1$ and $X^2$ are other elements; and
x is the number of oxygens required to satisfy the valence requirements of the other elements present.

6 Claims, No Drawings

CATALYST COMPOSITIONS AND THEIR USE FOR THE PREPARATION OF UNSATURATED CARBOXYLIC ACIDS

This is a division of application Ser. No. 499,108 filed May 27, 1983, now abandoned, which is a continuation-in-part of U.S. Ser. No. 385,365 filed June 7, 1982, now abandoned.

This invention relates to novel catalyst compositions for the preparation of unsaturated carboxylic acids by the vapor phase oxidation of unsaturated aldehydes. Unsaturated carboxylic acids include acrylic acid and methacrylic acid. Unsaturated aldehydes include acrolein and methacrolein.

There are many catalysts and also many procedures known for the preparation of acrylic acid and methacrylic acid and other unsaturated acids. The following is a list of patents which disclose one or the other: U.S. Pat. Nos. 3,761,516; 3,795,703; 3,773,692; 3,875,220; 3,998,876; 4,000,088; 4,051,179; 4,070,397 and 4,075,244. None of these patents discloses the specific process nor the specific compositions of this invention.

The novel catalysts are represented by the formula $$Mo_{12}P_aX^1_bV_cAs_dCu_eSb_fX^2_gO_x$$

wherein
- $X^1$ is one or more elements selected from cesium, thallium or rubidium;
- $X^2$ is one or more elements selected from tungsten, niobium, tantalum, zirconium, tin, zinc, iron, bismuth, boron, rhenium, tellurium, cobalt or potassium;
- a is a number in the range of from about 0.85 to about 1.2;
- b is a number in the range of about 0.75 to about 1.25;
- c is a number in the range of about 0.05 to about 0.7;
- d is a number in the range of about 0.5 to about 2.0;
- e is a number in the range of about 0 to about 0.4;
- f is a number in the range of about 0 to about 0.3;
- g is a number in the range of about 0 to about 2.0; and
- x is the number of oxygens required to satisfy the valence requirements of the other elements present.

Preferred catalyst compositions of this invention are those of the formula:

$$Mo_{12}P_{a'}Cs_bV_{c'}As_{d'}Cu_eSb_fX^2_gO_x$$

wherein
- a' is in the range of from about 1 to about 1.2;
- b is in the range of from about 1 to about 1.25;
- c' is in the range of from about 0.2 to about 0.7;
- d' is in the range of from about 0.5 to about 1.0;
- e is in the range of from about 0 to about 0.25;
- f is in the range of from about 0 to about 0.2;
- g is in the range of from about 0 to about 1.0; and
- $x^2$ is one or more elements selected from bismuth, tungsten, cobalt, zinc or tin and X is as defined above.

The most preferred catalyst compositions are those represented by the formula:

$$Mo_{12}P_{a'}Cs_{b'}V_{c''}As_dCu_{e''}Sb_{f''}O_x$$

wherein
- a' is in the range of from about 1 to about 1.2;
- b' is in the range from about 1 to about 1.25;
- c'' is in the range from about 0.2 to about 0.6;
- d' is in the range from about 0.5 to about 1;
- e'' is in the range from about 0.2 to about 0.25;
- f' is in the range from about 0.1 to about 0.2; and
- x is as defined above. Catalysts having this formula afford the highest yield of desired product.

The catalyst of this invention may be employed in the supported or unsupported form. If a support is employed, any known support, such as alumina, pumice, silica carbide, zirconia, silica, alumina-silica, perlite and the like, that are stable under the reaction conditions, may be employed. Alumina-silica is the preferred carrier.

We have found that by employing particular chemicals and particular calcining techniques we are able to obtain catalysts which yield conversion rates consistently in excess of 90% and selectivities consistently above 75%.

The process, in general, comprises preparing the catalyst by adding molybdenum trioxide to water followed by the addition of phosphoric acid. This reaction mixture is heated to a temperature in the range of from about 60° to about 95° C. for a period of time sufficient to form phosphomolybdic acid, usually at least one hour and, preferably, three hours. Other catalyst elements are incorporated into the catalyst by mixing their oxides or salts or compounds convertible on heating into oxides with aqueous molybdenum trioxide either before or after the addition of phosphoric acid and mixing with ammonium hydroxide. The reaction to form the uncalcined catalyst is essentially complete at this time. The water is removed conveniently by heating at a temperature in the range of from about 50° to about 70° C. which usually takes from 10 to 20 hours. Other methods of removing water may be employed such as spray drying and the like. Any remaining water is removed by well known methods such as by heating at a temperature in excess of 100° C. in a vacuum oven. We have found it convenient to remove the water at a temperature in the range of from about 160° to 170° C. in a vacuum oven for at least 4 hours.

Though not essential to the performance of the catalyst, for convenience in calcining and in loading the reactor tubes, the dried, uncalcined catalyst is crushed to a convenient size particle. We have arbitrarily chosen 8 to 18 mesh (ASTM Standard).

The dried catalyst is then heated to a temperature in the range of from about 350° to about 450° C. and preferably in the range of from 385° C., to 415° C. and most preferably at almost 400° C. wherein the calcining temperature is achieved as rapidly as possible and, preferably, no longer than about 1 hour and more preferably no longer than about 20 minutes.

Calcining is a thermal treatment of a catalyst precursor which causes a chemical or structural transformation of the precursor into a catalytically active form.

The best catalysts are those prepared employing molybdenum trioxide. Other sources of molybdenum such as ammonium heptamolybdate afforded poor catalysts. In addition, it has been found that vanadium is essential for activation and that arsenic and vanadium are necessary if the catalyst is to have a reasonable life.

We have found that potassium without cesium in the catalyst causes a decrease in activity as opposed to the employment of cesium alone or cesium and potassium.

In the process of the present invention a mixture of the organic feed, in vapor form, and molecular oxygen, optionally, in the presence of steam or other diluents, is contacted with a catalyst of the above composition at a temperature in the range of from about 290° to about 320° C. for a contact time sufficient to convert the feed mainly to acrylic or methacrylic acid. The contact time may vary from about 2 to about 6 seconds or more. The reaction can be conducted under atmospheric, superatmospheric or subatmospheric pressures. However, in general, pressures slightly above atmospheric are preferred, such as 10 psig.

Any source of oxygen may be employed in the process, but for economic reasons it is preferred that air be employed as the source of oxygen.

Diluents such as water, nitrogen, carbon dioxide and the like may be present in the reaction mixture.

In general, apparatus of the type suitable for carrying out oxidation reactions in the vapor phase may be employed in this process. The process may be conducted either continuously or intermittently. The catalyst bed may be a fixed-bed employing a large particulate or pelletized catalyst, in the alternative, a so-called "fluidized" bed of catalyst may be employed.

The products of the reaction may be recovered by any of the methods known to those skilled in the art. One such method involves scrubbing the effluent gases from the reactor with cold water or another appropriate solvent to remove the products of the reaction. The ultimate recovery of the product may be accomplished by conventional means, such as by distillation or solvent extraction.

The examples disclosed in the specific embodiments are representative of the process conditions and catalyst compositions that are suitable for the process of this invention. However, the scope of the invention is not to be limited by these examples.

General Reaction Equipment and Procedure

A one liter glass resin kettle is equipped with high torque air stirrer, glass shaft and bearing with paddle ¼ inch cut to fit, Other equipment includes a heating mantle, variable voltage heat control, 21 in. immersion thermometer, stainless steel seives (8 and 18 mesh) and catch pans.

The molybdenum trioxide/phosphoric acid slurry is prepared as follows: charge kettle with 800 ml deionized water, set air stirrer to create vortex, and set temperature to 40° C. Add weighed molybdenum when 40° C. is reached and then add phosphoric acid. Raise the temperature to 80° C. and stir 3 hours. Turn off the heat and add 300 ml water to the kettle, add the chemicals sequentially to the kettle, making sure previous chemical is dissolved. Add antimony pentachloride next to last (if used). Ammonium hydroxide is always added last. (All standard molybdenumtrioxide/phosphoric acid preparations contain ammonium hydroxide) When all chemicals have been added begin heating again to 55° C. to remove the water (overnight). Next day, if the catalyst precursor is not almost completely dry, increase the temperature to 65°–75° C. When dry, place in a vacuum oven for 4 hours at 160° C. Remove the dry material to a desiscator to cool. Grind the precursor with pestle and screen, 8-18 mesh material. Finally, calcine the 8-18 mesh catalyst precursor for 6 hours at about 400° C. with 1 l/min air flow through catalyst bed to afford active catalyst.

CATALYST EXAMPLES

Example 1

$Mo_{12}P_1Cs_1V_{0.2}As_1Sb_{0.1}$

To 800 ml of deionized water is added molybdenum trioxide (120.9 grams). This reaction mixture is heated to 40° C. at which time is added phosphoric acid (8.07 grams). This mixture is stirred for three hours at 80° C. at which time there is added water (300 ml), cesium nitrate (13.64 grams), ammonium metavanadate (1.64 grams), arsenic pentoxide (8.28 grams), antimony pentachloride (2.09 grams) and 29.2% ammonium hydroxide (12.25 grams). The reaction mixture is stirred for 16 hours at 57° C. and for 2.87 hours at 80° C. The catalyst precursor is collected and dried in the vacuum oven four hours at reduced pressure (15 mmHg) at 165° C. to afford 150.2 grams of catalyst precursor. The material is ground with a pestle directly on to sieves to yield 106.9 grams of 8–18 mesh material and 43 grams of fines. The catalyst precursor is calcined for 6 hours at 400° C. with an air flow of 1 liter/minute to afford active catalyst.

Example 2

$Mo_{12}P_1Cs_1V_{0.2}As_1Cu_{0.2}Sb_{0.1}$

To 800 ml of water is added molybdenum trioxide (120.9 grams). The reaction mixture is warmed to 40° C. and phosphoric acid (8.07 grams) is added. The reaction mixture is stirred for three hours at 80° C. and then water (300 ml), cesium nitrate (13.64 grams), ammonium vanadate (1.64), arsenic pentoxide (8.28 grams); cuprous nitrate (3.26 grams), antimony pentachloride (2.09 grams) and 29.2% ammonium hydroxide (12.25 grams) are added. The reaction mixture is stirred at 55° C. for 16.75 hours and at 80° C. for 4.25 hours. The catalyst precursor is collected and dried in a vacuum oven for 4 hours at 165° C. at reduced pressure (10 mmHg) to yield 148 grams. The catalyst precursor is ground with a pestle to afford 93.0 grams of 8–18 mesh material and 54.9 grams of fines. Calcining of the 93 grams for 6 hours at 400° C. with an air flow of 1 liter per minute yields 86.9 grams of active catalyst.

Example 3

$Mo_{12}P_{1.2}Cs_{1.25}V_{0.4}As_{0.7}Cu_{0.25}Sb_{0.2}$

To 800 ml of water is added molybdenum trioxide (120.9 grams), arsenic pentoxide (5.8 grams) and cupric nitrate (4.07 grams). The reaction mixture is heated to 40° C. There is then added phosphoric acid (9.69 grams) and the reaction mixture heated for 3 hours at 80° C. at which time additional water (350 ml) and ammonium meta vanadate (3.28 grams), antimony pentachloride (4.19 grams), cesium nitrate (17.05 grams) and ammonium hydroxide (12.25 grams) are added. The reaction mixture is stirred for 17 hours at 80° C. The catalyst precursor is collected and dried in a vacuum oven for 4.5 hours at 165° C. at reduced pressure (30 mmHg) to yield 153.9 grams. The catalyst precursor is ground with a pestle to afford 102.5 grams of 8–18 mesh material and 50.7 grams of fines. The 102.5 grams is calcined for 6 hours at 400° C. with an airflow of 1 liter per minute to afford 87.8 grams of 8–18 mesh material and 9.6 grams of fines.

Example 4

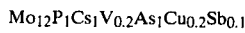

To 800 ml of water is added molybdenum trioxide (120.9 grams). The mixture is heated to 40° C. and phosphoric acid (8.07 grams) is added. This mixture is then heated for 3 hours at 80° C. Additional water (300 ml) and cesium nitrate (13.64 grams), ammonium vanadate (1.64 grams); arsenic pentoxide (8.28 grams), cupric nitrate (3.26 grams), antimony pentachloride (2.09 grams) and ammonium hydroxide (12.5 grams) are added. The reaction mixture is stirred for 17.3 hours at 55° C. and 2.75 hours and 80° C. The catalyst precursor is collected and dried for 4.5 hours at 165° C. at reduced pressure (5 mmHg) to yield 149.1 grams of catalyst precursor. The precursor is ground to 4 mesh and calcined for 6 hours at 400° C. with an airflow of 1 liter per minute to afford 140.8 grams of active catalyst.

Example 5

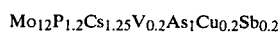

By following the general procedure and employing 120.9 grams of molybdenum trioxide, 9.69 grams phosphoric acid, 17.05 grams of cesium nitrate, 16.4 grams of ammonium vanadate, 8.28 grams of arsenic pentoxide, 3.26 grams of coppr nitrate, 4.19 grams of antomony pentachloride and 12.5 grams of ammonium hydroxide, there is obtained, after drying at 4.5 hours at 100° C. at reduced pressure (5 mmHg) and for 5 hours at 165° C. at reduced pressure, 135.0 grams of dried material which after grinding affords 79.2 grams of 8–18 mesh material and 55.4 grams of fines. The 8–18 mesh materials is calcined for 6 hours at 400° C. with an airflow of 1 liter per minute to afford 75.1 grams of active catalyst.

By employing substantially the procedures described above and by employing the following amounts of ingredients, (numbers refer to grams of material) there are obtained additional active catalysts as shown in Examples 6–10.

STANDARD SCREENING PROCEDURE

Pack 20.0 to 25 grams of the catalyst in a ⅜" stainless steel U-tube. Reactor catalyst volume is approximately 20.0 cc. Immerse the tube in a salt bath for temperature control. Feed a mixture of air, nitrogen, water, and methacrolein over the catalyst. The water is vaporized in the air stream and the methacrolein is vaporized in the nitrogen stream. Desired conditions are as follows:

Salt bath temperature—300° C.
Total flow rate—1004 mmol/hr (corresponds to 3.2 sec. space time)
Reactor pressure—10.0 psig
Air flow—479.2 mmol/hr
Nitrogen flow—183.4 mmol/hr
Methacrolein flow—40.0 mmol/hr
$H_2O$ flow—301.4 mmol/hr Reactor effluent analyzed for acetaldehyde, acetone, acrolein, methacrolein, acetic acid, acrylic acid, and methacrylic acid by on line gas chromatography. Noncondensable gases analyzed by gas partitioning for $CO_2$, $O_2$, $N_2$, and CO. Condensed effluent is titrated for total acidity. It can also be analyzed by GLC if necessary; particularly, for calibration purposes. A gaseous sample of effluent is automatically injected in to the online analytical system every 35 minutes, intergration performed, and results calculated by computer from analytical data, flow rates, temperatures, and pressures. Averages and standard deviations for conversions, selectivities and accountabilities are computed for each run using valid samples with accountabilities of approximately 90% to 105%. The first samples of each evaluation run are omitted from this calculation.

The following tables illustrates the composition and catalytic activity of some of the catalysts of this application. However, all catalysts embraced by the generic formula prepared by the method described in this application are expected to behave in a similar manner.

TABLE I

Catalyst Compositions

| Example No. | Mo | P | Cs | V | As | Cu | Sb | X |
|---|---|---|---|---|---|---|---|---|
| 1 | 12 | 1.0 | 1.0 | 0.2 | 1.0 | — | 0.1 | — |
| 2 | 12 | 1.0 | 1.0 | 0.2 | 1.0 | 0.2 | 0.1 | — |
| 3 | 12 | 1.2 | 1.25 | 0.4 | 0.7 | 0.25 | 0.2 | — |
| 4 | 12 | 1.0 | 1.0 | 0.2 | 1.0 | 0.2 | 0.1 | — |
| 5 | 12 | 1.2 | 1.25 | 0.2 | 1.0 | 0.2 | 0.2 | — |
| 6 | 12 | 1.2 | 1.25 | 0.2 | 1.0 | 0.2 | 0.2 | — |
| 7 | 12 | 1.2 | 1.25 | 0.6 | 0.5 | — | 0.2 | — |
| 8 | 12 | 1.5 | 1.25 | 0.2 | 1.0 | 0.2 | — | $W_{0.5}Co_{0.5}Zn_{0.5}$ |
| 9 | 12 | 1.2 | 1.25 | 0.6 | 0.7 | 0.2 | 0.2 | — |
| 10 | 12 | 1.2 | 1.25 | 0.4 | 0.25 | 0.2 | — | — |
| 11 | 12 | 1.15 | 0.75 | 0.05 | 1.7 | 0.3 | — | — |
| 12 | 12 | 1.0 | 1.0 | 0.2 | 1.0 | 0.2 | — | — |
| 13 | 12 | 1.15 | 1.25 | 0.05 | 1.3 | 0.3 | — | — |
| 14 | 12 | 1.0 | 1.0 | 0.2 | 1.6 | 0.2 | — | — |
| 15 | 12 | 1.0 | 1.0 | 0.2 | 1.5 | 0.2 | — | — |
| 16 | 12 | 1.1 | 1.12 | 0.3 | 0.85 | 0.2 | 0.15 | — |
| 17 | 12 | 1.0 | 1.0 | 0.2 | 1.4 | 0.2 | — | — |
| 18 | 12 | 1.0 | 1.0 | 0.2 | 1.0 | 0.2 | — | $Bi_{0.2}$ |
| 19 | 12 | 1.0 | 1.0 | 0.2 | 1.4 | 0.2 | 0.1 | — |
| 20 | 12 | 1.1 | 1.12 | 0.3 | 0.85 | 0.1 | 0.15 | — |
| 21 | 12 | 1.0 | 1.2 | 0.45 | 0.6 | 0.15 | — | — |
| 22 | 12 | 1.05 | 1.0 | 0.2 | 1.5 | 0.2 | — | — |
| 23 | 12 | 1.0 | 1.0 | 0.2 | 1.6 | 0.2 | — | — |
| 24 | 12 | 1.0 | 1.0 | 0.2 | 1.0 | 0.2 | 0.1 | $W_{1.0}$ |
| 25 | 12 | 1.0 | 1.0 | 0.2 | 1.0 | 0.2 | 0.1 | $Te_{0.1}Sn_{0.1}$ |
| 26 | 12 | 1.1 | 1.0 | 0.2 | 1.5 | 0.2 | — | — |

| Ex. No. | $MoO_3$ | $H_3PO_4$ | $CsNO_3$ | $NH_4VO_3$ | $As_2O_5$ | $SbCl_5$ | $NH_4OH$ (28.5%) | Other |
|---|---|---|---|---|---|---|---|---|
| 6 | 120.9 | 9.7 | 17.05 | 1.64 | 8.28 | 4.19 | 12.5 | 3.26 $Cu(NO_3)_2$ |
| 7 | 120.9 | 9.7 | 17.05 | 4.92 | 4.14 | 4.18 | 12.5 | — |
| 8 | 120.9 | 12.1 | 20.46 | 1.64 | 8.28 | — | 12.5 | 3.26 $Cu(NO_3)_2$ 7.26 $Zn(NO_3)_2$ 8.1 $WO_3$ 10.2 $Co(NO_3)_2$ |
| 9 | 120.9 | 12.1 | — | 1.64 | 8.28 | — | 12.5 | 5.3 $KNO_3$ 3.26 $Cu(NO_3)_2$ 8.1 $WO_3$ 10.2 $Co(NO_3)_2$ |
| 10 | 120.9 | 9.7 | 17.05 | 4.92 | 5.8 | 4.18 | 12.5 | 3.26 $Cu(NO_3)_2$ |

TABLE I-continued

Catalyst Compositions

| Example No. | Mo | P | Cs | V | As | Cu | Sb | X |
|---|---|---|---|---|---|---|---|---|
| 27 | 12 | 1.1 | 1.12 | 0.3 | 0.85 | 0.1 | 0.2 | — |
| 28 | 12 | 1.0 | 1.0 | 0.2 | 1.0 | 0.2 | — | $Bi_{0.1}$ |
| 29 | 12 | 1.0 | 1.0 | 0.2 | 1.0 | 0.2 | 0.1 | $Nb_{0.2}$ |
| 30 | 12 | 1.1 | 1.12 | 0.3 | 0.85 | 0.1 | 0.1 | — |
| 31 | 12 | 1.0 | 1.25 | 0.2 | 1.0 | 0.2 | 0.2 | — |
| 32 | 12 | 1.0 | 1.0 | 0.2 | 1.0 | 0.2 | 0.1 | $Te_{0.1}$ |
| 33 | 12 | 1.1 | 1.12 | 0.2 | 0.85 | 0.1 | 0.15 | — |
| 34 | 12 | 1.1 | 1.25 | 0.3 | 0.55 | 0.25 | 0.15 | — |
| 35 | 12 | 1.15 | 0.75 | 0.35 | 1.3 | 0.3 | — | — |
| 36 | 12 | 1.2 | 1.0 | 0.2 | 1.0 | 0.2 | 0.2 | — |
| 37 | 12 | 1.0 | 1.0 | 0.2 | 1.0 | 0.3 | 0.1 | — |
| 38 | 12 | 1.0 | 1.0 | 0.2 | 1.0 | 0.4 | 0.1 | — |
| 39 | 12 | 1.1 | 1.4 | 0.6 | 0.8 | 0.3 | — | — |
| 40 | 12 | 1.0 | 1.0 | 0.2 | 1.0 | 0.2 | 0.1 | $W_{0.5}$ |
| 41 | 12 | 1.1 | 1.35 | 0.3 | 0.55 | — | 0.15 | — |
| 42 | 12 | 1.0 | 1.0 | 0.2 | 1.0 | 0.2 | 0.05 | — |
| 43 | 12 | 0.85 | 1.25 | 0.05 | 1.3 | 0.3 | — | — |
| 44 | 12 | 1.2 | 1.25 | 0.6 | 0.7 | 0.2 | 0.2 | — |
| 45 | 12 | 1.0 | 1.0 | 0.2 | 1.0 | 0.2 | 0.2 | — |
| 46 | 12 | 1.0 | 1.12 | 0.3 | 0.85 | 0.1 | 0.15 | — |
| 47 | 12 | 1.2 | 1.25 | 0.2 | 1.0 | 0.2 | 0.1 | — |
| 48 | 12 | 1.0 | 1.0 | 0.2 | 1.0 | 0.2 | 0.1 | $Ta_{0.2}$ |
| 49 | 12 | 1.0 | 1.0 | 0.2 | 1.8 | 0.2 | — | — |
| 50 | 12 | 1.2 | 1.12 | 0.3 | 0.85 | 0.1 | 0.15 | — |
| 51 | 12 | 1.0 | 0.5 | 0.2 | 1.0 | 0.2 | 0.1 | $k_{0.5}$ |
| 52 | 12 | 1.0 | 1.25 | 0.4 | 0.7 | 0.2 | 0.2 | — |
| 53 | 12 | 1.1 | 1.12 | 0.4 | 0.85 | 0.1 | 0.15 | — |
| 54 | 12 | 1.0 | 0.75 | 0.2 | 1.4 | 0.2 | — | — |
| 55 | 12 | 1.0 | 1.2 | 1.0 | 0.2 | 0.1 | — | — |
| 56 | 12 | 1.15 | 0.75 | 0.05 | 1.3 | 0.1 | — | — |
| 57 | 12 | 1.2 | 1.25 | 0.4 | 0.7 | 0.25 | 0.05 | — |
| 58 | 12 | 1.0 | 0.5 | 0.2 | 1.4 | 0.2 | — | — |
| 59 | 12 | 1.05 | 1.25 | 0.3 | 0.55 | — | 0.15 | — |
| 60 | 12 | 0.85 | 0.75 | 0.35 | 1.3 | 0.1 | — | — |
| 61 | 12 | 0.9 | 1.0 | 0.2 | 1.5 | 0.2 | — | — |
| 62 | 12 | 1.0 | 1.0 | 0.2 | 1.0 | 0.2 | 0.1 | — |
| 63 | 12 | 1.0 | 1.25 | 0.2 | 1.4 | 0.2 | — | — |
| 64 | 12 | 1.2 | — | 0.2 | 1.0 | 0.2 | 0.2 | $Ti_{1.25}$ |
| 65 | 12 | 1.2 | 1.0 | 0.2 | 1.5 | 0.2 | — | — |
| 66 | 12 | 1.1 | 1.0 | 0.3 | 0.85 | 0.1 | 0.15 | — |
| 67 | 12 | 1.2 | 1.0 | 0.4 | 0.7 | 0.2 | 0.1 | — |
| 68 | 12 | 1.2 | 1.25 | 0.4 | 0.7 | — | 0.2 | — |
| 69 | 12 | 1.1 | 1.12 | 0.3 | 1.0 | 0.1 | 0.15 | — |
| 70 | 12 | 1.1 | 1.25 | 0.3 | 0.85 | 0.1 | 0.15 | — |
| 71 | 12 | 1.2 | 1.25 | 0.4 | 0.7 | 0.25 | — | — |
| 72 | 12 | 1.0 | 1.0 | 0.2 | 1.0 | 0.2 | 0.1 | $B_{0.3}$ |
| 73 | 12 | 1.0 | 1.0 | 0.2 | 1.0 | 0.1 | 0.1 | — |
| 74 | 12 | 1.0 | 1.0 | 0.2 | 1.0 | 0.2 | 0.1 | $W_{2.0}$ |
| 75 | 12 | 1.2 | 1.25 | 0.18 | 0.7 | — | 0.2 | — |
| 76 | 12 | 1.2 | 1.25 | 0.8 | 0.4 | 0.2 | 0.2 | — |
| 77 | 12 | 1.0 | 1.0 | 0.2 | 0.2 | 0.2 | — | — |
| 78 | 12 | 1.1 | 1.12 | 0.3 | 0.7 | 0.1 | 0.15 | — |
| 79 | 12 | 1.0 | 1.0 | 0.6 | 0.85 | 0.2 | 0.1 | — |
| 80 | 12 | 1.15 | 0.75 | 0.35 | 1.7 | 0.1 | — | — |
| 81 | 12 | 1.0 | — | 0.2 | 1.0 | 0.2 | 0.1 | $Tl_{1.0}$ |
| 82 | 12 | 1.0 | 1.0 | 0.2 | 1.0 | — | — | — |
| 83 | 12 | 1.0 | 1.0 | 0.2 | 1.2 | 0.2 | — | — |
| 84 | 12 | 1.2 | 1.25 | 0.4 | 0.7 | 0.25 | 0.1 | — |
| 85 | 12 | 1.0 | 1.0 | 0.2 | 1.0 | 0.5 | 0.1 | — |
| 86 | 12 | 1.0 | 1.0 | 0.2 | 1.1 | 0.2 | — | — |
| 87 | 12 | 1.0 | 1.25 | 0.2 | 0.7 | 0.2 | 0.1 | — |
| 88 | 12 | 1.15 | 1.25 | 0.35 | 1.3 | 0.1 | — | — |
| 89 | 12 | 1.0 | 1.25 | 0.4 | 1.0 | — | 0.1 | — |
| 90 | 12 | 1.0 | — | 0.2 | 1.0 | 0.2 | 0.1 | $Rb_1$ |
| 91 | 12 | 1.2 | 1.25 | 0.4 | 0.7 | 0.05 | 0.2 | — |
| 92 | 12 | 1.0 | 0.2 | 1.0 | 0.2 | 0.1 | — | — |
| 93 | 12 | 1.2 | 1.25 | 0.5 | 0.5 | — | 0.2 | — |
| 94 | 12 | 1.0 | 1.0 | 0.2 | 1.0 | 0.2 | 0.1 | $Re_{0.01}$ |
| 95 | 12 | 1.15 | 1.25 | 0.05 | 1.7 | 0.1 | — | — |
| 96 | 12 | 1.2 | 1.25 | 0.5 | 0.6 | — | 0.2 | — |
| 97 | 12 | 1.0 | 1.0 | 0.2 | 1.0 | 0.2 | 0.1 | $W_{0.3}Nb_{0.3}$ |
| 98 | 12 | 1.1 | 1.25 | 0.3 | 0.55 | — | 0.1 | — |
| 99 | 12 | 1.1 | 1.45 | 0.3 | 0.55 | — | 0.15 | — |
| 100 | 12 | 1.0 | 1.0 | 0.2 | 1.0 | 0.2 | 0.1 | $Zr_{0.2}$ |
| 101 | 12 | 1.2 | 1.25 | 0.4 | 1.0 | 0.2 | 0.1 | — |
| 102 | 12 | 1.2 | 1.0 | 0.2 | 0.7 | 0.2 | 0.2 | — |
| 103 | 12 | 1.0 | 1.0 | 0.2 | 0.7 | — | 0.2 | — |

TABLE II

CATALYTIC ACTIVITY

| Ex. No. | Conversion (%) | Selectivity (%) | Yield of Methacrylic Acid (%) |
|---|---|---|---|
| 2 | 99.2 | 82.8 | 82.1 |
| 3 | 92.1 | 87.1 | 80.2 |
| 5 | 99.5 | 80.9 | 80.5 |
| 6 | 99.0 | 79.5 | 78.7 |
| 7 | 88.9 | 83.2 | 73.9 |
| 9 | 90.3 | 87.2 | 78.7 |
| 10 | 93.4 | 86.8 | 81.1 |
| 11 | 96.4 | 86.3 | 83.2 |
| 12 | 96.4 | 86.1 | 83.0 |
| 13 | 97.8 | 84.8 | 82.9 |
| 14 | 98.0 | 83.7 | 82.0 |
| 15 | 98.6 | 85.2 | 84.0 |
| 16 | 94.9 | 84.7 | 80.4 |
| 17 | 95.5 | 86.6 | 82.7 |
| 18 | 98.4 | 82.8 | 81.5 |
| 19 | 96.7 | 86.4 | 83.5 |
| 20 | 97.1 | 82.1 | 79.7 |
| 21 | 99.3 | 77.9 | 77.4 |
| 22 | 96.5 | 85.7 | 82.7 |
| 23 | 93.5 | 88.5 | 82.7 |
| 24 | 98.1 | 83.7 | 82.1 |
| 25 | 98.1 | 81.4 | 79.9 |
| 26 | 99.0 | 81.7 | 80.9 |
| 27 | 91.8 | 87.1 | 80.0 |
| 28 | 94.1 | 83.9 | 78.9 |
| 29 | 98.5 | 82.3 | 81.1 |
| 30 | 96.6 | 83.4 | 80.6 |
| 31 | 91.8 | 87.0 | 79.9 |
| 32 | 96.8 | 83.5 | 80.8 |
| 33 | 99.0 | 78.2 | 77.4 |
| 34 | 99.3 | 77.1 | 76.6 |
| 35 | 87.5 | 88.7 | 77.6 |
| 36 | 97.7 | 81.7 | 79.8 |
| 37 | 97.4 | 82.2 | 80.1 |
| 38 | 94.5 | 83.1 | 78.5 |
| 39 | 96.8 | 83.3 | 80.6 |
| 40 | 99.4 | 78.4 | 77.9 |
| 41 | 96.8 | 80.1 | 77.5 |
| 42 | 99.1 | 77.5 | 76.8 |
| 43 | 97.3 | 83.3 | 81.1 |
| 44 | 90.3 | 87.2 | 78.7 |
| 45 | 99.8 | 72.2 | 72.1 |
| 46 | 92.0 | 86.7 | 79.8 |
| 47 | 98.7 | 79.4 | 78.4 |
| 48 | 98.4 | 81.5 | 80.2 |
| 49 | 84.8 | 89.8 | 76.2 |
| 50 | 88.6 | 87.0 | 77.1 |
| 51 | 90.3 | 86.4 | 78.0 |
| 53 | 88.7 | 88.1 | 78.1 |
| 53 | 93.4 | 86.3 | 80.6 |
| 54 | 99.3 | 79.2 | 78.6 |
| 55 | 98.7 | 79.4 | 78.4 |
| 56 | 98.1 | 80.2 | 78.7 |
| 57 | 98.0 | 81.0 | 79.4 |
| 58 | 97.7 | 82.0 | 80.1 |
| 59 | 88.6 | 82.6 | 73.2 |
| 60 | 95.0 | 81.0 | 77.0 |
| 61 | 90.7 | 87.1 | 79.0 |
| 62 | 99.8 | 77.0 | 76.8 |
| 63 | 99.6 | 77.9 | 77.6 |
| 64 | 98.9 | 76.9 | 76.1 |
| 65 | 90.8 | 87.7 | 79.6 |
| 66 | 98.7 | 79.5 | 78.5 |
| 67 | 97.4 | 79.9 | 77.8 |
| 68 | 89.9 | 89.3 | 80.3 |
| 69 | 91.8 | 86.1 | 79.0 |
| 70 | 94.6 | 84.4 | 79.8 |

TABLE II-continued
CATALYTIC ACTIVITY

| Ex. No. | Conversion (%) | Selectivity (%) | Yield of Methacrylic Acid (%) |
|---|---|---|---|
| 71 | 99.6 | 75.8 | 75.5 |
| 72 | 92.3 | 86.1 | 79.5 |
| 73 | 98.9 | 76.0 | 75.2 |
| 74 | 92.5 | 83.9 | 77.6 |
| 75 | 87.1 | 82.0 | 71.4 |
| 76 | 84.0 | 88.4 | 74.3 |
| 77 | 99.5 | 76.4 | 76.0 |
| 78 | 98.6 | 78.8 | 77.7 |
| 79 | 82.6 | 89.9 | 74.3 |
| 80 | 82.4 | 89.6 | 73.8 |
| 81 | 97.9 | 80.0 | 78.3 |
| 82 | 98.3 | 79.7 | 78.3 |
| 83 | 92.3 | 81.4 | 75.1 |
| 84 | 96.4 | 79.9 | 77.0 |
| 85 | 95.9 | 80.3 | 77.0 |
| 86 | 99.4 | 75.9 | 75.4 |
| 87 | 99.9 | 74.1 | 74.0 |
| 88 | 82.8 | 89.5 | 74.1 |
| 89 | 84.6 | 84.3 | 71.3 |
| 90 | 95.5 | 78.0 | 74.5 |
| 91 | 90.1 | 86.1 | 77.6 |
| 92 | 99.7 | 72.6 | 72.4 |
| 93 | 84.4 | 84.6 | 71.4 |
| 94 | 97.8 | 78.5 | 76.8 |
| 95 | 78.1 | 91.1 | 71.1 |
| 96 | 85.2 | 84.3 | 71.8 |
| 97 | 99.7 | 74.6 | 74.4 |
| 98 | 97.0 | 73.6 | 71.4 |
| 99 | 91.7 | 80.4 | 73.7 |
| 100 | 89.3 | 82.3 | 73.5 |
| 101 | 87.5 | 86.4 | 75.6 |
| 102 | 99.7 | 69.8 | 69.6 |
| 103 | 97.6 | 74.7 | 72.9 |

Comparison of Catalysts of This Invention with Known Catalysts

PREPARATION OF CATALYSTS OF THIS INVENTION: Five batches of catalyst were prepared by the following procedure. In a 1 lb. resin kettle equipped with overhead air-driven stirrer, thermometer, temperature controller and heating mantle add 120.9 g of $MoO_3$ (0.840 mole) to 800 ml of deionized water. Heat to 40° C. and add 8.07 g of 85% $H_3PO_4$ (0.070 mole). Heat to 80° C. and hold at this temperature for 3 hours. Stop heating and replace evaporated water, then add sequentially 13.64 g of $CsNO_3$ (0.070 mole), 1.64 g of $NH_4VO_3$ (0.014 mole), 8.28 g of $As_2O_5$ (0.035 mole), 3.26 g of $Cu(NO_3)_2.2.5H_2O$ (0.014 mole), 2.09 g of $SbCl_5$ (0.007 mole), and 3 moles of concentrated $NH_4OH$ for every 12 moles of $MoO_3$ (0.021 mole). Heat at 55° C. for 17 hours then increase temperature to 80° C. to evaporate remaining water. Dry at 165° C. for 4 hours at a pressure of 50 torr to give 148.2 g. Calcine at 400° C. for 6 hours. Grind to powder—yield 139.3 g. Add 1% graphite by weight and pelletize to $\frac{1}{8} \times \frac{1}{8}''$ pellets. Catalyst of Example numbers 104, 105, 106, 107 and 108 were prepared in this manner. The composition of these catalysts is $Mo_{12}P_1Cs_1V_{0.2}As_1Cu_{0.2}Sb_{0.1}O_x$ (or in the terms of U.S. Pat. No. 4,051,179; $Mo_1P_{0.083}Cs_{0.083}V_{0.017}As_{0.083}Cu_{0.017}Sb_{0.0083}O_x$).

PREPARATION OF KNOWN CATALYST: Example 1 from U.S. Pat. No. 4,051,179. In the apparatus used in Examples 104–108 place 250 ml of deionized water and 88.5 g of ammonium heptamolybdate (0.0716 mole). Heat to 60° C. and add 4.8 g of 85% $H_3PO_4$ (0.0416 mole) and 7.1 g of 50% aqueous $H_3AsO_4$ (0.025 mole), then add 2.02 g of $Cu(NO_3)_2.3H_2O$ (0.00836 mole) in 50 ml of deionized water, 2.44 g of $NH_4VO_3$ (0.0209 mole) in 75 ml of deionized water, add 4.22 g of $KNO_3$ (0.0417 mole) and 5.37 g of $Mg(NO_3)_2.6H_2O$ (0.0209 mole) in 50 ml of deionized water. Stir at 60° C. for 20 hours. Dry at 130° C. (1 atm) for 16 hours to yield 99.5 g of dry material. Grind to powder and add 2% stearic acid and 1% graphite by weight. Pelletize to $\frac{1}{8} \times \frac{1}{8}''$ and calcine in a programmed furnace increasing the temperature by 20° C. per hour from 100° to 400° C. and holding at 400° C. for 5 hours. Five catalysts were made by this procedure and designated K-1, K-2, K-3, K-4 and K-5. The composition of these catalysts is $Mo_1P_{0.083}As_{0.05}V_{0.042}K_{0.083}Mg_{0.042}O_x$.

EVALUATION: Catalysts were evaluated by placing about 22.5 g of catalyst in a $\frac{3}{8}''$ stainless steel tube and passing a feed with a $O_2:N_2:H_2O$:Methacrolein ratio of 10:65:20:5 over the catalyst with a space time of about 3.6 sec. The feed was at a pressure of 8 psig. The reactor was held at 290° C. with a molten salt bath. Samples of effluent were periodically evaluated by an on-line gas chromatograph and an on-line gas partitioner. One obvious physical difference between catalysts of this invention and those made according to the patent procedure is that the catalysts of this invention are about 30% denser than the other catalysts.

RESULTS: The average conversion, selectivity, and yield of each catalyst is given in Table III. The mean results and their standard deviations were also calculated for each of the preparation and are presented in Table IV. A test of statistical significance at the 95% confidence level indicates that the catalysts of this invention have a significantly higher conversion and yield than the patent example catalysts.

CONCLUSION: The data show that the catalysts of this invention are superior to the known catalysts of example 1 of U.S. Pat. No. 4,051,179.

TABLE III

| EXAMPLE | CONV | SEL | YIELD |
|---|---|---|---|
| 104 | 99.1 | 75.2 | 74.5 |
| 105 | 99.4 | 69.6 | 69.2 |
| 106 | 99.3 | 72.6 | 72.1 |
| 107 | 99.2 | 68.4 | 67.9 |
| 108 | 99.3 | 74.7 | 74.2 |
| K-1 | 63.2 | 81.8 | 51.7 |
| K-2 | 60.6 | 80.6 | 48.8 |
| K-3 | 51.5 | 83.1 | 42.8 |
| K-4 | 22.7 | 84.1 | 19.1 |
| K-5 | 64.4 | 82.1 | 52.9 |

TABLE IV

| VARIABLE | N | MEAN | STANDARD DEVIATION |
|---|---|---|---|
| CATALYSTS OF EXS. 104–108 | | | |
| CONV | 5 | 99.26 | 0.11401754 |
| SEL | 5 | 72.10 | 3.02324329 |
| YIELD | 5 | 71.58 | 2.95245660 |
| KNOWN CATALYSTS | | | |
| CONV | 5 | 52.48 | 17.39790217 |
| SEL | 5 | 82.34 | 1.32778010 |
| YIELD | 5 | 43.06 | 13.95145154 |

What is claimed is:

1. A catalyst of the formula $Mo_{12}P_{a'}Cs_{b'}V_{c''}As_{d'}Cu_{e''}Sb_{f'}O_x$ wherein $a'$ is in the range of from about 1 to about 1.2;
  $b'$ is in the range of from about 1 to about 1.25;
  $c''$ is in the range of from about 0.2 to about 0.6;
  $d'$ is in the range of from about 0.5 to about 1.0;
  $e''$ is in the range of from about 0.2 to about 0.25;

f″ is in the range of from about 0.1 to about 0.2; and x is the number of oxygens required to satisfy the valence requirements of the other elements present, prepared by suspending molybdenum trioxide in water followed by the addition of phosphoric acid, heating to a temperature in the range of from about 60° to about 95° C. for at least 1 hour, mixing the remaining elements at their oxides or salts or compounds convertible on heating into the oxides with aqueous molybdenum trioxide either before or after the addition of phosphoric acid, mixing with ammonium hydroxide, isolating the material and calcining at a temperature in the range of from about 350° to about 450° C.

2. The catalyst prepared according to claim 1 of the formula; $Mo_{12}P_1Cs_1V_{0.2}As_1Cu_{0.2}Sb_{0.1}O_x$.

3. The catalyst prepared according to claim 1 of the formula; $Mo_{12}P_{1.1}Cs_{1.12}V_{0.3}As_{0.85}Cu_{0.2}Sb_{0.15}O_x$.

4. The catalyst prepared according to claim 1 of the formula; $Mo_{12}P_{1.2}Cs_{1.25}V_{0.2}As_{1.0}Cu_{0.2}Sb_{0.1}O_x$.

5. The catalyst prepared according to claim 1 of the formula; $Mo_{12}P_{1.2}Cs_{1.25}V_{0.2}As_{1.0}Cu_{0.2}Sb_{0.1}O_x$.

6. The catalyst prepared according to claim 1 of the formula; $Mo_{12}P_{1.2}Cs_{1.25}V_{0.6}As_{0.5}Sb_{0.2}O_x$.

* * * * *